United States Patent
Ekin

(10) Patent No.: US 11,589,929 B2
(45) Date of Patent: Feb. 28, 2023

(54) ASSESSING DEVICE FOR ASSESSING AN INSTRUMENT'S SHAPE WITH RESPECT TO ITS REGISTRATION SUITABILITY

(71) Applicant: KONINKLIJKE PHILIPS N.V., Eindhoven (NL)

(72) Inventor: Ahmet Ekin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 70 days.

(21) Appl. No.: 17/040,570

(22) PCT Filed: Mar. 26, 2019

(86) PCT No.: PCT/EP2019/057477
§ 371 (c)(1),
(2) Date: Sep. 23, 2020

(87) PCT Pub. No.: WO2019/185563
PCT Pub. Date: Oct. 3, 2019

(65) Prior Publication Data
US 2021/0059767 A1 Mar. 4, 2021

(30) Foreign Application Priority Data
Mar. 27, 2018 (EP) .................................... 18164305

(51) Int. Cl.
*A61B 34/20* (2016.01)
*G06T 7/50* (2017.01)
(Continued)

(52) U.S. Cl.
CPC ................ *A61B 34/20* (2016.02); *G06T 7/50* (2017.01); *G06T 7/73* (2017.01); *G16H 40/40* (2018.01);
(Continued)

(58) Field of Classification Search
CPC .......... A61B 34/20; A61B 6/12; A61B 5/065; A61B 6/487; A61B 2034/2065;
(Continued)

(56) References Cited

U.S. PATENT DOCUMENTS

2014/0264081 A1* 9/2014 Walker .................. A61B 6/586
250/206.1
2015/0124264 A1  5/2015 Ramachandran
(Continued)

FOREIGN PATENT DOCUMENTS

WO  2014053934   4/2014
WO  2015/044930  4/2015
(Continued)

OTHER PUBLICATIONS

International Search Report and Written Opinion dated Jun. 4, 2019 for International Application No. PCT/EP2019/057477 Filed Mar. 26, 2019.

*Primary Examiner* — Brenda C Bernardi

(57) ABSTRACT

The invention relates to an assessing device (13) for assessing the suitability of a shape of an instrument like a guidewire for a registration of a position and shape determination device (10) like an optical shape sensing device with an imaging device (2). Curvature values being indicative of the curvature at several positions along the instrument are determined, which are used for determining shape feature values. These shape feature values are then used for determining a suitability value being indicative of the suitability of the shape of the instrument for the registration procedure, wherein an output is provided to a user based on the determined suitability value. The user can therefore modify the shape until the output indicates that the shape of the instrument is suitable for the registration, without requir- (Continued)

ing any image. This can reduce a radiation dose if the image is, for instance, an x-ray image.

13 Claims, 7 Drawing Sheets

(51) Int. Cl.
    *G06T 7/73*     (2017.01)
    *G16H 40/40*     (2018.01)
    *A61B 90/00*     (2016.01)

(52) U.S. Cl.
    CPC ........... *A61B 2034/2061* (2016.02); *A61B 2034/2065* (2016.02); *A61B 2090/3764* (2016.02); *G06T 2207/30004* (2013.01)

(58) Field of Classification Search
    CPC . A61B 2576/00; A61B 5/6852; A61B 6/4441; A61B 2090/376; A61B 2090/3764; A61B 2034/2061; G16H 40/40; G16H 30/40; G06T 7/73; G06T 7/50; G06T 2207/30004

See application file for complete search history.

(56) References Cited

U.S. PATENT DOCUMENTS

| | | |
|---|---|---|
| 2015/0254526 A1 | 9/2015 | Denissen |
| 2016/0202053 A1* | 7/2016 | Walker ............... G01B 11/24 250/227.14 |
| 2016/0253804 A1 | 9/2016 | Ekin |
| 2017/0100084 A1 | 4/2017 | Walker |

FOREIGN PATENT DOCUMENTS

| | | |
|---|---|---|
| WO | 2015/062898 | 5/2015 |
| WO | 2016116821 | 7/2016 |
| WO | 2016116825 | 7/2016 |

* cited by examiner

ASSESSING DEVICE FOR ASSESSING AN INSTRUMENT'S SHAPE WITH RESPECT TO ITS REGISTRATION SUITABILITY

CROSS REFERENCE TO RELATED APPLICATIONS

This application is the U.S. National Phase application under 35 U.S.C. § 371 of International Application No. PCT/EP2019/057477 filed Mar. 26, 2019, which claims the benefit of European Patent Application Number 18164305.7 filed Mar. 27, 2018. These applications are hereby incorporated by reference herein.

FIELD OF THE INVENTION

The invention relates to an assessing device, method and computer program for assessing a suitability of a shape of an instrument for performing a registration procedure. The invention relates further to an interventional system for performing an image-guided interventional procedure and a corresponding interventional method, and to a registration method and computer program for registering a position and shape determination device for determining a position and shape of an instrument with an imaging device for generating an image of the instrument.

BACKGROUND OF THE INVENTION

In order to guide a physician during an interventional procedure, an imaging device like an x-ray C-arm device can be used which provides images showing an interventional instrument within a subject. Moreover, a position and shape determination device can be used for determining the position and shape of the interventional instrument within the subject, wherein the position and shape determination device can be, for instance, an optical shape sensing device. In order to properly guide the physician during the interventional procedure, it is required to register the position and shape determination device with the imaging device, wherein a resulting registration transformation can be used to generate overlay images in which a representation of the instrument in its determined position and shape is overlaid over the images generated by the imaging device. The registration is carried out in a registration procedure which is performed before the actual interventional procedure is started, i.e. the registration procedure is especially carried out before the interventional instrument is introduced into the subject. For the registration a user like the physician or another person prepares at least the interventional instrument, i.e. he/she positions the interventional instrument and optionally changes its shape and then acquires a first image while the imaging device is in a first position and a second image while the imaging device is in a second position. Based on these acquired first and second images and a determination of the current position and shape by the position and shape determination device the imaging device and the position and shape determination device are registered to each other. If the preparation for the registration was not good enough for providing an accurate registration result, the entire registration procedure including the preparation must be repeated, which prolongs the registration process, or the guidance for the physician during the actual interventional procedure would be relatively inaccurate.

SUMMARY OF THE INVENTION

It is an object of the present invention to provide an assessing device, method and computer program for assessing a shape of an instrument, which allows for a shorter accurate registration process. It is a further object of the present invention to provide an interventional system and an interventional method for performing an image-guided interventional procedure, and to provide a registration method and computer program for registering a position and shape determination device for determining a position and shape of an instrument with an imaging device for generating an image of the instrument.

In a first aspect of the present invention an assessing device for assessing a shape of an instrument is presented, wherein the assessing device is configured to assess a suitability of the shape of the instrument for performing a registration procedure, wherein the shape has been determined by a position and shape determination device and wherein the registration procedure relates to a registration of the position and shape determination device with an imaging device for imaging the instrument, wherein the assessing device comprises:

a feature determination unit configured to determine first shape feature values which depend on the shape (and optionally the position) of the instrument (which may be provided to the assessing device, via e.g. an input of the assessing device), wherein the feature determination unit is configured to determine curvature values being indicative of the curvature at several positions along the instrument and to determine the first shape feature values based on the curvature values, a suitability value determination unit configured to determine a first suitability value being indicative of the suitability of the shape of the instrument for the registration procedure based on the determined first shape feature values, an output unit for providing an output to a user based on the determined first suitability value.

Since the suitability value determination unit determines the first suitability value being indicative of the suitability of the shape of the instrument for the registration procedure based on the determined first shape feature values and since the output unit provides an output to a user based on the determined first suitability value, after the user has positioned and set the shape of the instrument as desired for the registration, information can be provided immediately, which indicates to the user whether the actual shape of the instrument would lead to an accurate registration result. If this is not the case, the user can modify the shape of the instrument. Thus, the user can modify the shape of the instrument until the assessing device indicates to the user that the shape of the instrument will lead to an accurate registration result. Since the indication is given right at the beginning of the registration procedure, i.e. before a registration device starts with a calculation of a registration transformation for registering the position and shape determination device with the imaging device, the accurate registration can be ensured with no significant increase of the time needed for the entire registration procedure. Moreover, since for the assessment of the suitability of the shape of the instrument for performing the registration procedure no images are required, this fast ensured accurate registration can be provided with a relatively low radiation dose, if the imaging device uses radiation for the imaging procedure which is generally the case, especially if the imaging device is an x-ray imaging device.

Preferentially, the suitability value determination unit is configured to determine the first suitability value such that it indicates a suitability class of a group of predefined suitability classes, which are indicative of different degrees of suitability of a shape of an instrument for the registration procedure, based on the determined first shape feature value, wherein a first suitability class indicates that the shape is not suitable and a second suitability class indicates that the shape is suitable, wherein the output unit is configured to provide different outputs for different suitability classes. Thus, the predefined suitability classes include at least a first suitability class indicating that the shape is not suitable and a second suitability class indicating that the shape is suitable, wherein the predefined suitability classes can also include further, intermediate suitability classes indicating an intermediate degree of suitability. For instance, a third, intermediate suitability class can be predefined. The output unit can be adapted to provide different colors for the different predefined suitability classes. For instance, for the first suitability class a red color can be output, for the second suitability class a green color can be output and, if present, for the third suitability class a yellow color can be output. Also other colors can be assigned to the different suitability classes. It is also possible to assign other kinds of outputs to the different suitability classes like different acoustical signals.

In an embodiment the suitability value determination unit is configured to store the shape together with the determined suitability class such that, if the assessing device has been used with different shapes, different previous shapes together with corresponding previous suitability classes are stored, wherein the output unit is configured to show a representation of a stored previous shape together with the corresponding previous suitability class to the user. For instance, for each suitability class or for one or several certain suitability classes like the first suitability class and/or the second suitability class, the latest stored previous shape can be shown by the output unit, i.e. a representation of this latest stored previous shape can be shown. Thus, in an embodiment not all previous shapes assigned to a certain suitability class might be stored, but only the latest previous shape assigned to the respective suitability class. If a representation of a previous shape, which has been assigned to a certain suitability class, is shown to the user, for instance, a good example and/or a bad example for a shape of the instrument can be shown to the user, wherein these examples can guide the user in modifying the shape of the instrument such that, for instance, the second suitability class, which indicates that a shape is suitable for the registration, is determined for the current shape. This can lead to an improved assisting of the user in finding a shape which is suitable for the registration.

The instrument has a distal part, a proximal part and an intermediate part between the distal part and the proximal part, wherein the feature determination unit is preferentially configured to determine curvature values being indicative of the curvature at several positions along the distal part of the instrument and to determine the first shape feature values based on these curvature values. By using not all curvature values along the entire instrument, but only curvature values along the distal part of the instrument, the computational effort for determining the first shape feature values and the first suitability value can be reduced, thereby further increasing the speed of providing the result of the assessment to the user.

Preferentially, the feature determination unit is configured such that the first shape feature values include at least one of a maximum curvature value and an orientation change value being indicative of a change of orientation along the instrument. It has been found that by using at least one of the maximum curvature value and the orientation change value for determining the first suitability value the accuracy of the assessment of the registration suitability of the current shape of the instrument can be further increased.

In a preferred embodiment the feature determination unit is configured, for determining the orientation change value, to a) determine orientation difference values being indicative of the orientation differences of portions of the instrument at locations along the instrument having a predetermined distance to each other, b) determine a first number being indicative of the number of orientation difference values above a predetermined first threshold, c) determine a second number being indicative of the number of orientation difference values above a predetermined second threshold, and d) determine the orientation change value based on the first number and the second number. Moreover, the feature determination unit is preferentially configured to determine the orientation change value depending on a weighted combination of the first number and the second number. It has been found that, if the orientation change value is calculated in this way, the accuracy of assessing the suitability of the current shape of the instrument for the registration can be even further increased.

The suitability value determination unit is preferentially configured to determine the first suitability value by comparing the first shape feature values with predefined shape feature value ranges. Since the comparison of the first shape feature values with the predefined shape feature value ranges can be carried out very fast, this kind of determining the first suitability value further increases the speed of providing an indication of the registration suitability for the current shape to the user. The predefined shape feature value ranges can be predetermined based on calibration measurements, wherein for many different shapes of an instrument the registration accuracy can be determined and these data can be used for predetermining the shape feature value ranges. For this predetermination, known machine learning algorithms can be used. The comparison with a predefined shape feature value range can also be a comparison with a single threshold, wherein in this case a range includes all values above or below the threshold.

It is also preferred that the assessing device is configured to assess a suitability of the shape of the instrument for performing a registration procedure for registering the position and shape determination device with a further position and shape determination device for determining the position and shape of a further instrument, wherein a) the feature determination unit is configured to determine curvature values being indicative of the curvature at several positions along the instrument and along the further instrument and to determine second shape feature values based on the curvature values of both instruments, b) the suitability value determination unit is configured to determine a second suitability value being indicative of the suitability of the shape of the instrument and of the further shape of the further instrument for the registration of the position and shape determination device with the further position and shape determination device based on the determined second shape feature values, and c) the output unit is configured to provide an output to the user based on the determined second suitability value. Thus, the assessing device cannot only be configured to assess the registration suitability for a registration of the position and shape determination device with the imaging device, but it can also be adapted to assess the registration suitability for a registration of the position and shape determination device for determining the position and shape of the instrument with another position and shape determination device for determining the position and shape of another instrument. For instance, the assessing device can be adapted to assess the suitability of the shapes of a guidewire and a catheter for a registration of a position and shape determination device used for the guidewire and a further position and shape determination device used for the catheter. Thus, it can be ensured that the two position and shape determination devices are accurately registered to each other, wherein also in this case the time required for the registration procedure is not significantly increased.

If the position and shape determination device for the instrument, i.e. the first position and shape determination device, is accurately registered with the imaging device and if the first position and shape determination device is accurately registered with the further position and shape determination device for the further instrument, i.e. with the second position and shape determination device, the position and orientation of the two instruments relative to each other and relative to the subject can be shown on an image of the inside of the subject provided by the imaging device.

The feature determination unit is preferentially configured such that the second shape feature values include at least one of a) a peakness strength value being indicative of a strength of a peak of a curvature match score, which is determined for different simulated relative positions of the instrument and hence its position and shape relative to the further instrument and hence its position and shape and which is indicative of a similarity of the curvature values of the instrument and the curvature values of the further instrument, b) a minimum curvature value as the minimum of the mean curvature values of the instrument and of the further instrument in an overlap region in which the instrument and the further instrument overlap, wherein the feature determination unit is configured to determine the overlap region based on the curvature values, c) a maximum curvature value as the maximum of the mean curvature values of the instrument and of the further instrument in the overlap region, and d) a total mean curvature value as the mean of the mean curvature values of the instrument and of the further instrument in the overlap region. It has been found that the accuracy of assessing the suitability of the current shape of the instrument for the registration of the first position and shape determination device with the second position and shape determination device can be increased, if these second shape feature values are used.

Preferentially, for determining the peak strength value, the feature determination unit is configured to a) determine the simulated relative position of the instrument relative to the further instrument at which the curvature match score is maximal, b) determine difference values between the maximum curvature match score and curvature match scores determined for relative positions having a distance to the maximum relative position for which the maximum curvature match score has been determined, which is smaller than a predefined distance, c) determine a first sum of the difference values which have been determined for the relative positions being smaller than the maximum relative position and a second sum of the difference values which have been determined for the relative positions being larger than the maximum relative position, and d) determine the smaller one of the first sum and the second sum as the peak strength value. It has been found that, if the peak strength value is determined in this way, the accuracy of assessing the registration suitability of the current shape of the instrument for a registration of the first position and shape determination device with the second position and shape determination device can be even further increased.

In a further aspect of the present invention an interventional system for performing an image-guided interventional procedure is presented, wherein the interventional system comprises:

an interventional instrument to be used within a subject, an imaging device constructed to image the interventional instrument within the subject, a position and shape determination device constructed to determine a position and shape of the interventional instrument within the subject, an assessing device constructed to assess a suitability of the shape of the interventional instrument for registering the position and shape determination device with the imaging device, as defined by claim 1, wherein the position and shape determination device and the assessing device are configured to determine at least the shape of the instrument and to assess the suitability of the shape of the instrument, while a user at least modifies the shape of the instrument, an input unit for allowing a user to indicate that a registration of the position and shape determination device with the imaging device should start based on the current determined position and shape, and a registration device for registering the position and shape determination device with the imaging device based on the current determined position and shape of the interventional instrument and based on an image showing the interventional instrument with the current determined position and shape, if the user has indicated that the registration should start.

The interventional system can comprise a further interventional instrument to be used within the subject and a further position and shape determination device constructed to determine a further position and shape of the further interventional instrument within the subject, wherein the assessing device can be constructed to assess a suitability of the shape of the interventional instrument and of the further shape of the further instrument for registering the position and shape determination device with the further position and shape determination device as defined in claim 7, wherein the registration device is constructed to register the position and shape determination device with the further position and shape determination device.

In another aspect of the present invention an assessing method for assessing a suitability of a shape of an instrument for performing a registration procedure is presented, wherein the shape has been determined by a position and shape determination device for determining a position and shape of an instrument and wherein the registration procedure relates to a registration of the position and shape determination device with an imaging device for imaging the instrument, wherein the assessing method comprises:

determining first shape feature values which depend on the shape of the instrument by a feature determination unit, wherein the feature determination unit determines curvature values being indicative of the curvature at several positions along the instrument and determines the first shape feature values based on the curvature values, determining a first suitability value being indicative of the suitability of the shape of the instrument for the registration procedure based on the determined first shape feature values by a suitability value determination unit, providing an output to a user based on the determined first suitability value by an output unit.

In an aspect of the present invention, a registration method for registering a position and shape determination device for determining the position and shape of an instrument with an imaging device for generating an image of the instrument is presented, wherein the registration method includes:

determining a position and shape of the instrument by using the position and shape determination device and assessing a suitability of the shape of the instrument for registering the position and shape determination device with the imaging device as defined in claim 12, while a user modifies at least the shape of the instrument, and allowing the user to indicate that the registration should start based on the current position and shape and registering the position and shape determination device with the imaging device, if the user has indicated that the registration should start based on the current position and shape.

In a further aspect of the present invention an assessing computer program for assessing a suitability of a shape of an instrument for performing a registration procedure is presented, the computer program comprising program code means for causing an assessing device as defined in claim 1 to carry out the steps of the assessing method as defined in claim 12, when the computer program is run on a computer controlling the assessing device.

In another aspect of the present invention a registration computer program for registering a position and shape determination device for determining the position and shape of an instrument with an imaging device for generating an image of the instrument is presented, the computer program comprising program code means for causing an interventional system as defined in claim 10 to carry out the steps of the registration method as defined in claim 13, when the computer program is run on a computer controlling the interventional system. Thus, the registration computer program can be configured such that it causes the position and shape determination device to determine the position and shape of the instrument and to cause the assessing device to assess the suitability of the shape of the instrument for registering the position and shape determination device with the imaging device, wherein these steps of determining the position and shape of the instrument and assessing the suitability of the shape of the instrument are repeated, while the user modifies the shape and optionally also the position of the instrument, wherein an output is provided to the user based on the current determined first suitability value, wherein, after the user has indicated that the current shape should be used for the registration, the registration device is caused to register the position and shape determination device with the imaging device.

It shall be understood that the assessing device, the interventional system, the assessing method, the registration method, the assessing computer program and the registration computer program have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
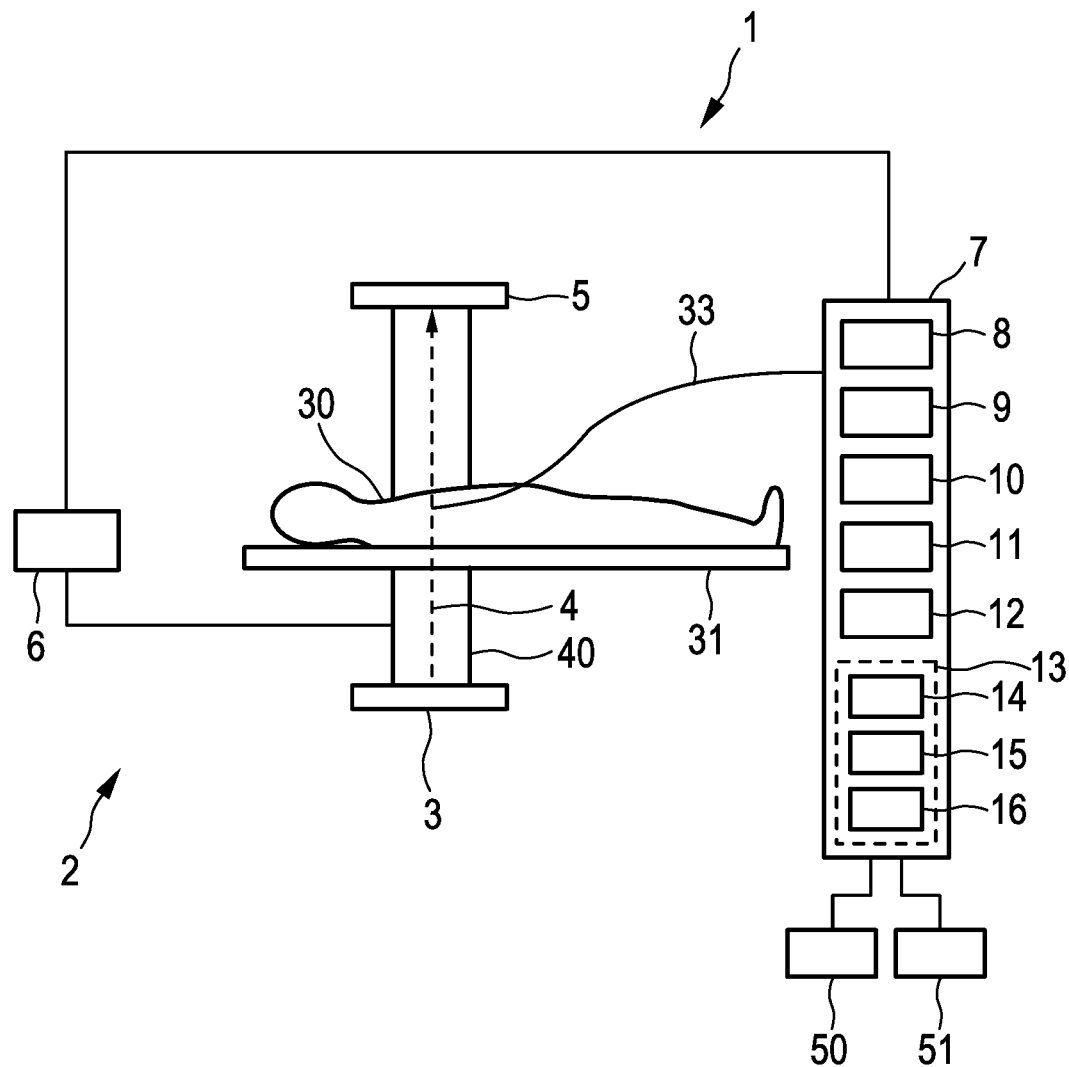
FIG. 1 shows schematically and exemplarily and embodiment of an interventional system for performing an image-guided interventional procedure.

FIG. 1 shows schematically and exemplarily an embodiment of an interventional system for performing an image-guided interventional procedure. In this embodiment the interventional system comprises an interventional instrument to be used within a subject 30, i.e. a patient, lying on a support means 31 like a support table. In this embodiment the interventional instrument is a guidewire within a catheter 33.

The interventional system 1 further comprises an imaging device 2 with a radiation source 3 for emitting x-rays 4 traversing the subject 3 and a detector 5 for detecting the x-rays 4 after having traversed the subject 30. The radiation source 3 and the detector 5 are mounted on a C-arm 40, wherein the imaging device 2 is adapted such that the C-arm 40 with the radiation source 3 and the detector 5 is rotatable relative to the support means 31. This ensures that x-ray images of the subject 30, which also show at least the tip of the guidewire, can be acquired in different acquisition directions. The C-arm 40, the radiation source 3 and the detector 5 are controlled by a control unit 6 which is also adapted to generate the x-ray images based on detection values received from the detector 5. The acquired x-ray images are transferred to a control and processing unit 7.

The interventional system 1 further comprises a position and shape control unit 8 for controlling the position and shape, i.e. the location, orientation and shape, of the guidewire. In this embodiment a user can provide an input indicating a desired position and shape of the guidewire via an input unit 50, whereafter the position and shape control unit 8 controls the guidewire accordingly such that it has the desired position and shape. The input unit 50 can be a keyboard, a touch pad, a joystick, et cetera. In another embodiment, the position and shape of the guidewire can also be set in another way. For instance, it can be simply directly set by the user manually. The interventional system 1 further comprises a position and shape determination device 10 constructed to determine the position and shape of the guidewire and an assessing device 13 constructed to assess a suitability of the current shape of the guidewire for registering the position and shape determination device 10 with the imaging device 2. The user can modify the shape of the guidewire, until the assessing device 13 indicates via an output unit 16 that the current position and shape of the guidewire will lead to an accurate registration, whereafter the position and shape determination device 10 can be registered with the imaging device 2 based on the current position and shape of the guidewire and an image generated by the imaging device 2, which shows the guidewire in its current position and shape.

The registration device 12 is adapted to detect the guidewire in an image generated by the imaging device 2 and to use this guidewire detection in the image together with the current position and shape of the guidewire as provided by the position and shape determination device 10 for registering the imaging device 2 with the position and shape determination device 10. The detection of the guidewire in the image can be carried out fully automatically, semi-automatically or fully manually, wherein for a semi-automatical or manual detection of the guidewire in the image the registration device 12 can be adapted to provide a graphical user interface via the input unit 50 and a further output unit 51 being preferentially a display. The output units 51 and 16 can be integrated, i.e. the entire system might comprise a single output unit fulfilling the functions of the described output units 51 and 16.

The assessing device 13 comprises a feature determination unit 14 configured to determine first shape feature values which depend on the position and shape of the guidewire, wherein the feature determination unit 14 is configured to determine curvature values being indicative of the curvature at several positions along the guidewire and to determine the first shape feature values based on the curvature values. The assessing device 13 further comprises a suitability value determination unit 15 configured to determine a first suitability value being indicative of the suitability of the current shape of the guidewire for the registration procedure based on the determined first shape feature values. The output unit 16 then provides an output, which might be an acoustical output and/or a visual output, to a user based on the determined first suitability value. For instance, the output unit 16 can be adapted to provide a red light, as long as the first suitability value indicates an insufficient suitability for the following registration, wherein, as soon as the first suitability value indicates a sufficient suitability for the following registration, the output unit 16 provides a green light. Hence, the suitability value determination unit 15 can be configured to determine the first suitability value such that it indicates a suitability class of a group of predefined suitability classes, which are indicative of different degrees of suitability of a shape of a guidewire for the registration procedure, based on the determined first shape feature value, wherein a first suitability class indicates that the shape is not suitable and a second suitability class indicates that the shape is suitable, wherein the output unit is configured to provide a red light, i.e. a red color, if the suitability value indicates the first suitability class, and a green light, i.e. a green color, if the suitability value indicates the second suitability class.

The guidewire has a distal part, a proximal part and an intermediate part between the distal part and the proximal part, wherein the feature determination unit 14 is configured to determine the curvature values being indicative of the curvature at several positions along the distal part of the guidewire and to determine the first shape feature values based on these curvature values. Thus, in this embodiment the determination of the first shape feature values and hence of the first suitability value is limited to the distal part of the guidewire. Moreover, the feature determination unit 14 is configured such that the first shape feature values include a maximum curvature value and an orientation change value being indicative of a change of orientation along the guidewire. The feature determination unit 14 determines the orientation change value by determining orientation difference values being indicative of the orientation differences of portions of the guidewire at locations along the distal part of the guidewire having a predetermined distance to each other, by determining a first number being indicative of the number of orientation difference values above a predetermined first threshold, by determining a second number being indicative of the number of orientation difference values above a predetermined second threshold and by determining the orientation change value based on the first number and the second number. In this embodiment, the feature determination unit 14 is configured to determine the orientation change value depending on a weighted combination of the first number and the second number. The predetermined first threshold, the predetermined second threshold and the weights for the weighted combination can be determined by calibration, wherein for many position, shape and image data registrations can be carried out and wherein the first threshold, the second threshold and the weights can be determined such that an accurate registration can be reliably predicted.

The interventional system 1 comprises a further interventional instrument to be used within the subject 30 together with the guidewire, wherein this further interventional instrument is the catheter 33 in this embodiment. The distal parts of the catheter 33 and the guidewire 32 are schematically and exemplarily illustrated in FIG. 2. It should be noted that in FIG. 2 the wave element 68 is just a graphical element which should indicate that the catheter 33 and the guidewire 32 are of course longer than indicated in FIG. 2, i.e. FIG. 2 really only shows the distal parts of the two instruments 32, 33.

The interventional system 1 comprises a further position and shape control unit 9 for controlling the position and shape, i.e. the location, orientation and shape, of the catheter. In this embodiment a user can provide an input indicating a desired position and shape of the catheter 33 via the input unit 50, whereafter the position and shape control unit 9 controls the catheter 33 accordingly such that it has the desired position and shape. In another embodiment the position and shape of the catheter 33 can also be set in another way. For instance, it can be simply directly set by the user manually.

The interventional system 1 comprises a further position and shape determination device 11 constructed to determine a position and shape of the catheter 33, wherein the assessing device 13 is constructed to further assess a suitability of the shape of the guidewire 32 and of the further shape of the catheter 33 for registering the position and shape determination device 10 with the further position and shape determination device 11. The further position and shape determination device 11 is, similar to the position and shape determination device 10, an optical shape sensing device being adapted for determining the further position and shape of the catheter 33 by optical shape sensing. The registration device 12 is constructed to also register the further position and shape determination device 11 with the position and shape determination device 10.

In order to assess the registration suitability for the registration of the position and shape determination device 10 with the further position and shape determination device 11, the feature determination device 14 is configured to determine curvature values being indicative of the curvature at several positions along the guidewire 32 and the catheter 33 and to determine second shape feature values based on these curvature values. Moreover, the suitability value determination unit 15 is configured to determine a second suitability value being indicative of the suitability of the shape of the guidewire 32 and of the shape of the catheter 33 for the registration of the position and shape determination device 10 with the further position and shape determination device 11 based on the determined second shape feature values. Furthermore, the output unit 16 is configured to provide an output to the user based on the determined second suitability value. Preferentially, the output unit is configured to provide an output based on the first suitability value and the second suitability value. For instance, both suitabilities can be indicated independently or a combined output can be provided. For instance, it can be indicated that the shapes are fine, if both suitability values indicate that both registrations can be carried out with a sufficient accuracy. The suitability values can be binary values, i.e. they can indicate that the accuracy is either sufficient or not sufficient, i.e. they can indicate one of two different suitability classes, or the suitability values can indicate more than two different suitability classes which might also be regarded as being different levels of expected or predicted registration accuracies.

The suitability value determination unit 15 is configured to determine the second suitability value by comparing the second shape feature values with predefined shape feature value ranges. Moreover, the suitability value determination unit 15 is configured to determine the first suitability value by comparing the first shape feature values with predefined shape feature value ranges. For different suitability values different shape feature value ranges can be predefined, wherein the suitability value determination unit 15 determines that a certain suitability value is present, if the determined shape feature values are within the corresponding predefined shape feature value ranges.

The feature determination unit 14 is configured such that the second shape feature values include at least one of a) a peakness strength value being indicative of a strength of a peak of a curvature match score, which is determined for different simulated relative positions of the guidewire 32 relative to the catheter 33 and which is indicative of a similarity of the curvature values of the guidewire 32 and the curvature values of the catheter 33, b) a minimum curvature value as a minimum of the mean curvature values of the guidewire 32 and of the catheter 33 in an overlap region in which the guidewire 32 and the catheter 33 overlap, wherein the feature determination unit 14 is configured to determine the overlap region based on the curvature values, c) a maximum curvature value as the maximum of the mean curvature values of the guidewire 32 and the catheter 33 in the overlap region, and d) a total mean curvature value as the mean of the mean curvature values of the guidewire 32 and the catheter 33 in the overlap region. Moreover, the feature determination unit 14 is configured i) to, for determining the peak strength value, determine the simulated relative position of the guidewire 32 relative to the catheter 33 at which the curvature match score is maximal, determine difference values between a) the maximum curvature match score and b) curvature match scores which have been determined for relative positions having a distance to the maximum relative position, for which the maximum curvature match score has been determined, which is smaller than a predefined distance, ii) to determine a first sum of the difference values which have been determined for the relative positions being smaller than the maximum relative position and a second sum of the difference values which have been determined for the relative positions being larger than the maximum relative position, and iii) to determine the smaller one of the first sum and the second sum as the peak strength value.

Figure 3:
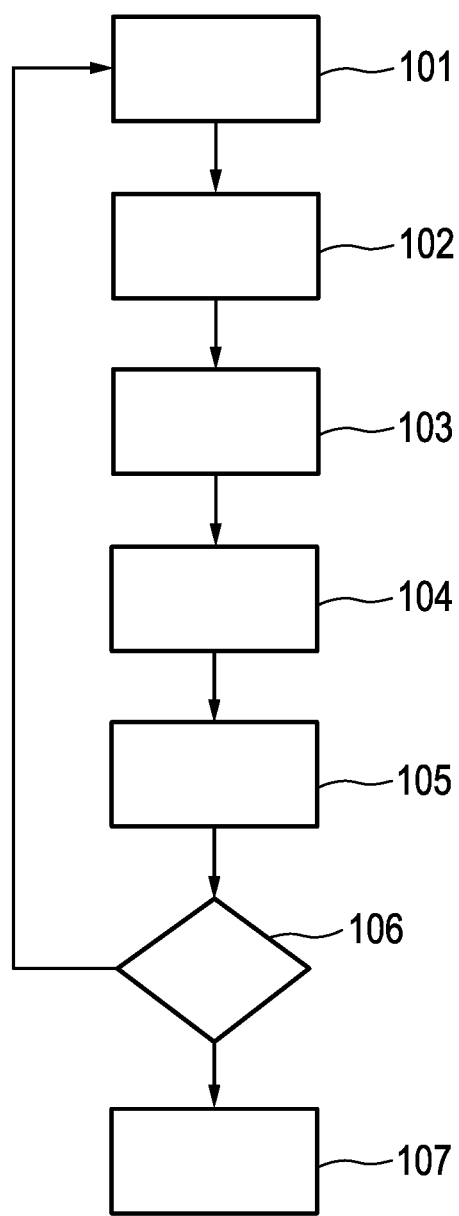
FIG. 3 shows a flowchart exemplarily illustrating an embodiment of a registration method.

In the following an embodiment of a registration method for registering a position and shape determination device for determining the position and shape of an instrument with an imaging device for generating an image of an instrument and for registering the position and shape determination device with a further position and shape determination device for determining a further position and shape of a further instrument will exemplarily be described with reference to a flowchart shown in FIG. 3.

In step 101 a user sets the shape of the guidewire 32 and the shape of the catheter 33 as desired. In step 102 the position and shape determination device 10 and the further position and shape determination device 11 determine the position and shapes of the guidewire 32 and of the catheter 33. In step 103 the feature determination unit 14 determines the first shape feature values and the second shape feature values and in step 104 the suitability value determination unit 15 determines the first suitability value being indicative of the suitability of the shape of the guidewire 32 for the registration of the position and shape determination device 10 with the imaging device 2 based on the determined first shape feature values and the second suitability value being indicative of the suitability of the shapes of the guidewire 32 and the catheter 33 for the registration between the position and shape determination device 10 and the further position and shape determination device 11 based on the determined second shape feature values. In step 105 an output is given to a user based on the determined first and second suitability values.

In step 106 it is determined whether the first and second suitability values indicate a sufficient suitability or not. For instance, if the suitability values can only have two values, i.e. if they are binary values indicating two different suitability classes, it is decided whether the respective binary value indicates a sufficient predicted registration accuracy or not. If at least one of the suitability values indicates an insufficient suitability, the method continues with step 101, i.e. the shapes of the instruments are modified and the suitability values are determined again. If the suitability values indicate a sufficient suitability, the registrations are carried out in step 107. Steps 101 to 107 can be carried out while the guidewire 32 and the catheter 33 are not within the subject, i.e. they can be carried out before the actual interventional procedure starts.

Although in above described embodiments the imaging device is an x-ray imaging device, especially a C-arm x-ray device, in other embodiments the imaging device can be another medical imaging modality like an ultrasound imaging modality.

The assessing device can be adapted to provide the user real time information about the suitability of one or several shapes of one or several instruments for shape related registration tasks like a registration between a position and shape determination device and an imaging device or a registration between different position and shape determination devices. The real time information helps the user in verifying the quality of the one or several shapes before starting the respective registration task. Moreover, since the assessing device is adapted to provide this information by computing features from only the respective shape, which is preferentially a three-dimensional shape, independently of the positioning of the imaging device, i.e. for instance, independently of a position of the C-arm x-ray device, the user can acquire the images only after the assessing device has approved the shape. This can lead to a reduced radiation dose.

Thus, a real time validation procedure can be provided, which is based on shape characteristics, especially based on optical shape sensing characteristics, and which provides the user with immediate information on the suitability of the one or several shapes of the one or several instruments for registration while the user is preparing the instruments for the subsequent registration procedure. The corresponding features can be calculated very fast and also the evaluation of the characteristics is very fast.

The output unit can be adapted to indicate which shape of which instrument needs to be modified, in order to have a successful subsequent registration. For instance, if the second suitability value indicates that the shapes are sufficient for accurately registering the different position and shape determination devices, but if the first suitability value indicates that the shape of the instrument, which should be used for the registration with the imaging device, will not lead to an accurate registration, the output unit can indicate that at least firstly only the shape of this instrument needs to be modified. The modification of the shape of this instrument then might lead to a change in the second suitability value, i.e. the second suitability value is preferentially determined again based on the modified shape of the instrument and the not-modified shape of the further instrument, wherein the output unit then indicates whether the second suitability value still indicates that the two shapes are suitable for the registration of the two position and shape determination devices with respect to each other. If this is not the case, it can be indicated to the user that the shape of the further instrument needs to be modified, i.e., for instance, by providing a representation of the shape of the further instrument on the output unit with a red color. Moreover, if the first suitability value indicates that the shape of the first instrument, i.e. of the guidewire in the above described embodiment, is suitable for the registration of the corresponding position and shape determination device with the imaging device, this can be indicated to the user via the output unit. For instance, a corresponding representation of the shape of the first instrument can be shown with a green color on the output unit. If in this situation the second suitability value indicates that with the present two shapes of the two instruments the registration between the position and shape determination devices would be inaccurate, it can be indicated to the user, as explained above, that the shape of the second instrument, i.e. in the above described embodiment of the catheter, needs to be modified. For instance, a representation of the shape of the second instrument might be shown in a red color.

The assessing device is adapted to extract curvature-derived features from one or several three-dimensional shapes and to use these extracted curvature-derived features for predicting the registration success. The assessing device is adapted to use for this prediction calculations which can be carried out with relatively low computational efforts such that the corresponding assessment result can be provided in real time and it can be provided before a single x-ray image or, if another imaging modality is used, another image is taken. This is very valuable, because it reduces the radiation dose.

For assessing the suitability of an instrument for a registration with an imaging device, preferentially only curvature values of the tip and of the most distal segment of the instrument are considered, because considering only these curvature values will reduce the computational efforts and in practice mostly the tip and the distal segment of the instrument are in the field of view of the imaging device during the registration procedure. The length of the most distal segment of the instrument, which might be a guidewire, can be determined by calibration, wherein for different lengths of the most distal segment the smallest length can be determined, which still leads to a reliable assessment of the suitability of the shape of the instrument for the subsequent registration. In an embodiment the length of the most distal segment is 25 cm.

The feature determination unit is adapted to determine the maximum curvature value, i.e. the maximum value of the curvature, and the orientation change value, which might also be named total strength of orientation change. The first feature is preferentially the maximum value of the curvature in the most distal segment of the respective position and shape. The second feature is preferentially the total strength of the orientation change. In an embodiment this total strength of orientation change is determined by computing the orientation difference between position and shape points that are N samples apart from each other, wherein the number N can be, for instance, 50 or it can have another value. It is then counted how many times the orientation difference is above predefined first and second thresholds of, for instance, 25 and 45 degrees, wherein the total strength of orientation change can be computed as a weighted combination, i.e. particularly as weighted sum, of these two counts. Thus, the first count can be weighted by using a first weighting factor and the second count can be weighted by using a second weighting factor, wherein these two weighted counts can be summed for determining the total strength of orientation change. The weights can be determined by calibration, wherein based on training data sets, for which it is known whether the respective training shapes are suitable or not suitable for a subsequent registration, the weights can be determined such that the respective suitability or non-suitability is reliably determined.

The orientation of the respective shape point, i.e. the orientation of the portion of the instrument at the respective location along the instrument, is also determined by the position and shape determination device based on the positions of the locations along the instrument which might be determined by, for instance, optical shape sensing. In particular, the position and shape determination device can be adapted to compute the derivatives of the locations along different axes of a coordinate system spanning the three-dimensional space, i.e., for instance, in an x direction, a y direction and a z direction. Thus, the position and shape determination device can be adapted to compute derivatives at each location in the three different directions, in order to compute a tangent vector, wherein the tangent vector at the respective location can be regarded as being a measure for the orientation at the respective location. An orientation difference can then be determined as being the angle between tangent vectors at different locations.

The suitability value determination unit can be adapted to use these two features, i.e. the maximum value of the curvature and the total strength of orientation change, for deciding on the suitability of a shape for, this embodiment, shape to x-ray registration, i.e. for registering the position and shape determination device with the imaging device. This decision on suitability can be made by checking whether the maximum value of the curvature and the total strength of orientation change are in predefined acceptable regions which could also be named ranges. If both are within the acceptable regions, the first suitability value might be one or might have another value indicating the suitability for the subsequent registration and, if not both features are within the acceptable regions, the first suitability value can be zero or can be another value indicating the non-suitability for the subsequent registration. This exemplary decision rule can be based on a learning algorithm which finds the acceptable regions by learning. The suitability value determination unit can also be adapted to use a decision tree for determining whether the current shape is suitable for the subsequent registration and for then assigning a corresponding number to the first suitability value. Also, the decision tree can be predetermined by using a learning algorithm, wherein the learning, which could also be named training, is based on a relatively large amount of data with samples of shapes and respective registration accuracies. After learning, the decision rule can be adapted such that, for instance, a relatively high total orientation change or a relatively high maximum curvature leads to a positive suitability assessment. The decision rule can also be adapted such that the current shape is approved for the subsequent registration, if the total strength of orientation change and the maximum value of the curvature have medium values.

In the embodiment described above with reference to, for instance, FIG. 2 the guidewire 32 is physically inside the catheter 33, wherein their position and shape data, i.e. in this embodiment their optical shape sensing data, should be visualized overlaid on an image generated by the imaging device 2. Regarding the registration between the position and shape determination devices 10, 11, the registration carried out by the registration device 12 preferentially uses an overlap region between the two instruments 32, 33. The overlap region indicates how much of the guidewire 32 is inside the catheter 33 and what parts of these instruments 32, 33 are overlapping.

Figure 2:
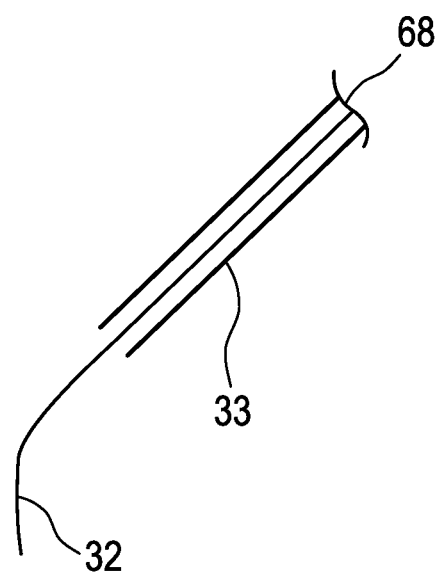
FIG. 2 illustrates schematically and exemplarily distal segments of a guidewire and of a catheter partly enclosing the guidewire.

In some cases, the guidewire tip protrudes the catheter 33 such that the whole catheter 33 defines the overlap region. Such a situation is illustrated in FIG. 2. In other cases, the guidewire tip can be inside the catheter 33 and correspondingly the overlap region is smaller. It is assumed that in the overlap region the curvature values of the first instrument, i.e. in this embodiment of the guidewire 32, and of the further second instrument, i.e. in this embodiment of the catheter 33, are similar, i.e. generally not exactly the same, because, for instance, the guidewire might have some freedom to bend relative to the catheter and vice versa, even if the guidewire is within the catheter, and/or because the fibers used for optical shape sensing and hence measuring the curvature might be differently arranged within the guidewire and the catheter. Thus, the feature determination unit is preferentially configured to determine a first region along the first instrument and a second region along the second instrument such that the first region and the second region have the same length and the curvature values in these two regions are similar. The feature determination unit determines the first region along the first instrument and the second region along the second instrument as the overlap region. For determining whether the curvature values are similar in these two regions any curvature similarity measure can be used, which depends on the degree of similarity of the curvature values in the first and second regions. If the curvature similarity measure provides a curvature similarity value being larger than a predefined threshold, it can be assumed that the curvature values in these two regions are similar. For instance, a curvature similarity measure can define that squared differences of curvature values at corresponding locations in the respective regions, i.e. at first locations along the first region and the second region, at second locations along the first region and the second region, at third locations along the first region and the second region, et cetera, are summed up, wherein the resulting sum can be divided by the number of locations considered in the two regions and wherein, in order to increase with increasing similarity, the resulting sum can be, for instance, multiplied by −1 or subtracted from some value. However, also other curvature similarity measures can be used.

Figure 4:
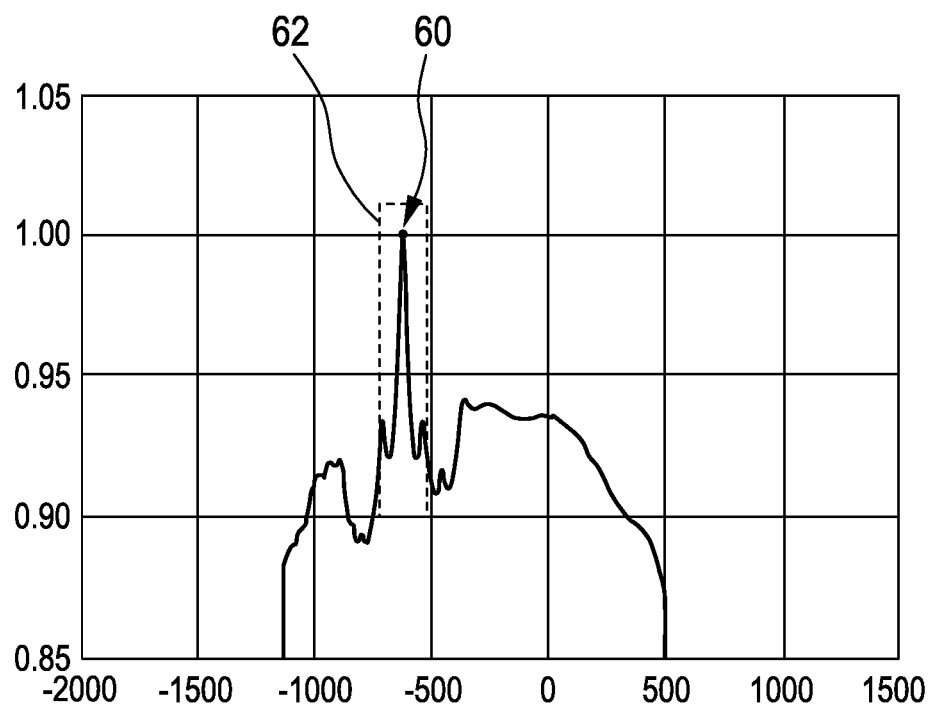
FIG. 4 shows schematically and exemplarity curvature match scores for different relative positions of a catheter with respect to a guidewire for first shapes of the catheter and the guidewire.
Figure 5:
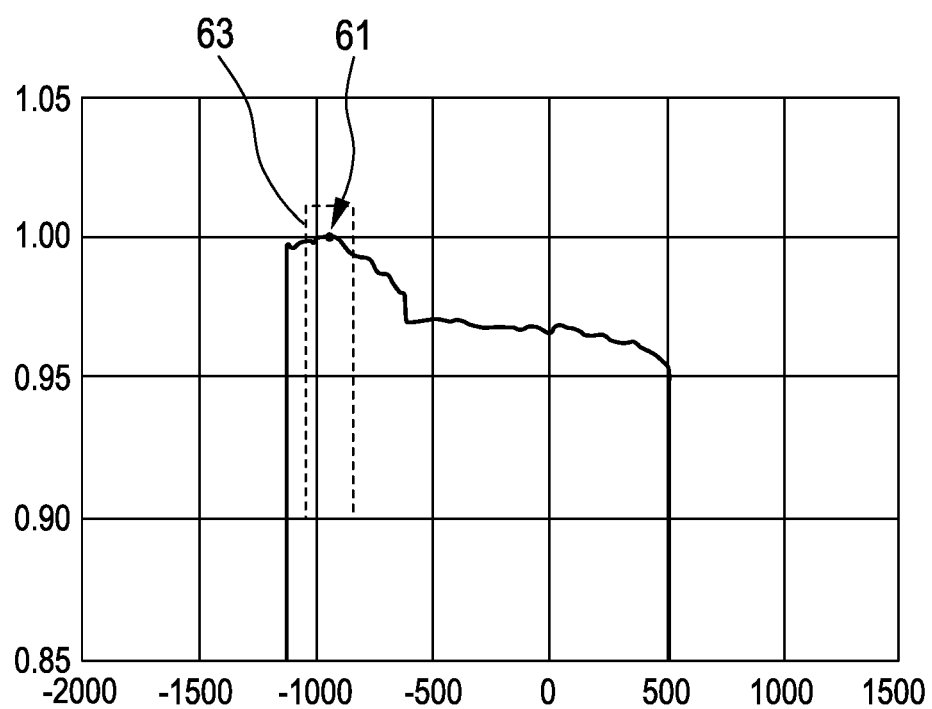
FIG. 5 shows exemplarily curvature match scores for different relative positions of the catheter with respect to a guidewire for second shapes of the catheter and the guidewire.

For calculating a peak strength value, the feature determination unit is adapted to determine from all candidate shifts, i.e. for all of different simulated relative positions of the guidewire and hence its shape relative to the catheter 33 and hence its shape, the maximum curvature similarity measure, i.e. the maximum curvature match score. In an example the scores are normalized to the maximum score so that each score lies in [0,1] as illustrated in FIGS. 4 and 5. In FIGS. 4 and 5 the vertical axis indicates the respective score and the horizontal axis indicates the respective candidate shift, i.e. the respective relative position, in arbitrary units. In FIGS. 4 and 5 the respective maximum score is indicated by the respective point 60, 61 and the number of candidate shifts, which is a predefined number of 50 in this example, is constant for this curvature match score procedure. The feature determination unit is adapted to determine the strength of the peak, i.e. of the maximum score 60, 61, in comparison to the scores of the other candidate shifts, wherein the result is the peak strength value. Thus, the feature determination unit is adapted to determine as the peak strength value a value which is indicative of the height of the peak, i.e. of the maximum score 60, 61, in comparison to the scores of the other candidate shifts. In a specific embodiment a region of interest is defined around the respective maximum score 60, 61. In FIGS. 4 and 5 this region of interest is indicated by the boxes 62, 63. The peakness strength value is then calculated based on the score values within the respective region of interest 62, 63.

The dimensions of the region of interest 62, 63 can be predefined and determined in advance based on a calibration procedure and a learning algorithm as described above. In a specific embodiment the differences of the scores from the peak value 60, 61, which has been normalized to a value of 1, are calculated. The sum of these scores on the left side and on the right side of the peak position are then determined and the minimum of these two scores is then determined as the peakness strength value. This can be described by following equations:

$$P_{right} = \sum_{k=max\ Ind+1}^{max\ Ind+100} (1 - M(k)), \quad (1)$$

$$P_{left} = \sum_{k=max\ Ind-100}^{max\ Ind-1} (1 - M(k)) \text{ and} \quad (2)$$

$$PeaknessStrength = \min(P_{left}, P_{right}), \quad (3)$$

wherein max Ind refers to the index for the candidate shift at the maximum position 60, 61 and wherein the width of the region of interest is set to include 100 samples, i.e. phase shifts, to the left and to the right of the max Ind index. Moreover, in equations (1) and (2) M(k) indicates the normalized score, i.e. the normalized curvature match score, at the respective candidate shift k.

The peakness strength value for the situation illustrated in FIG. 4 is 6.07 and for the situation illustrated in FIG. 5 0.18, i.e. the peakness strength value is much larger in the situation illustrated in FIG. 4 than in the situation illustrated in FIG. 5.

The feature determination unit is adapted to determine further second shape feature values based on the curvature values in the overlap region. These further second shape features are preferentially the maximum curvature and the mean curvature in the overlap region for both, i.e. for the guidewire and for the catheter that are to be registered to each other. In a specific embodiment the curvature values in the overlap region are used for computing mean curvatures for the guidewire 32 and the catheter 33. These two mean curvatures are then combined for providing the further second shape features. As the further second shape features the minimum of these two mean curvatures, the maximum of these two mean curvatures and the mean of these two mean curvatures can be determined.

These second shape features, i.e., for instance, at least two of the peakness strength value, the minimum of the two mean values, the maximum of the two mean values and the mean of the two mean values, are preferentially used to provide information about the suitability of the shapes of the guidewire 32 and the catheter 33 for the shape-to-shape registration, i.e. for the registration of the two position and shape determination devices with respect to each other.

Figure 6:
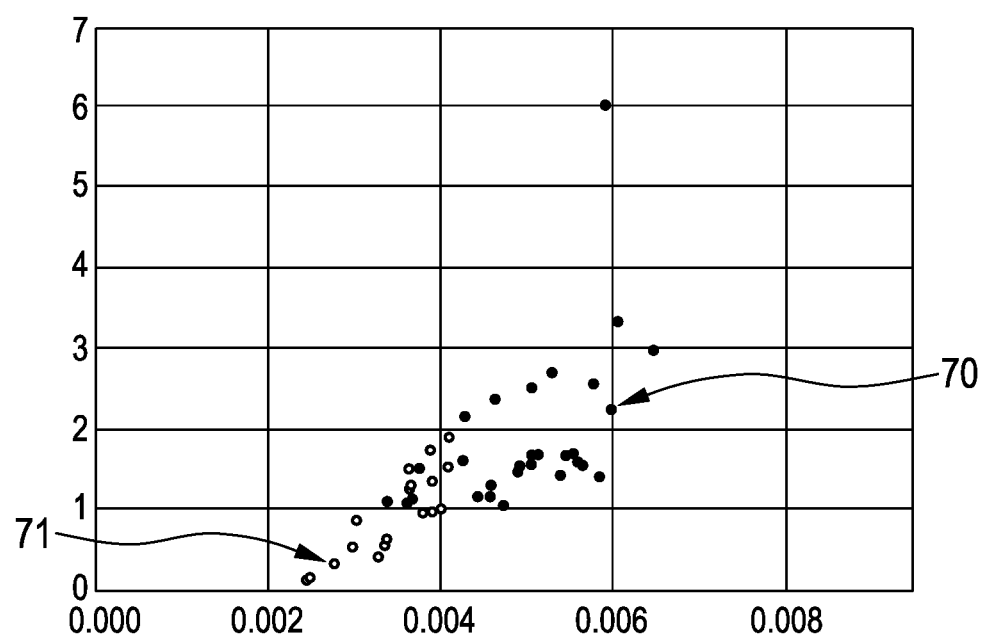
FIG. 6 illustrates exemplarily good registration results and bad registration results for different peakness strength values and different mean curvature values.

FIG. 6 exemplarily illustrates data obtained during a calibration procedure, wherein the filled dots 70 indicate good registration results, i.e. robust registrations, and the unfilled dots 71 indicate bad registrations, i.e. non-unique registrations. In FIG. 6 on the vertical axis the peakness strength value is shown and on the horizontal axis the average of the two mean curvature values determined for the overlap region for the guidewire and the catheter are indicated. As can be seen in FIG. 6, if for current shapes of the guidewire 32 and the catheter 33 an average of the means is determined, which is larger than, for instance, 0.0045, these position and shapes are likely suitable for the shape-to-shape registration. Moreover, if the peakness strength value is larger than, for instance, 2.0, the likelihood can be even larger that the shapes are suitable for the shape-to-shape registration. These thresholds can be determined automatically or by a person carrying out the calibration procedure and these thresholds can then later be used for determining the second suitability value.

Figure 7:
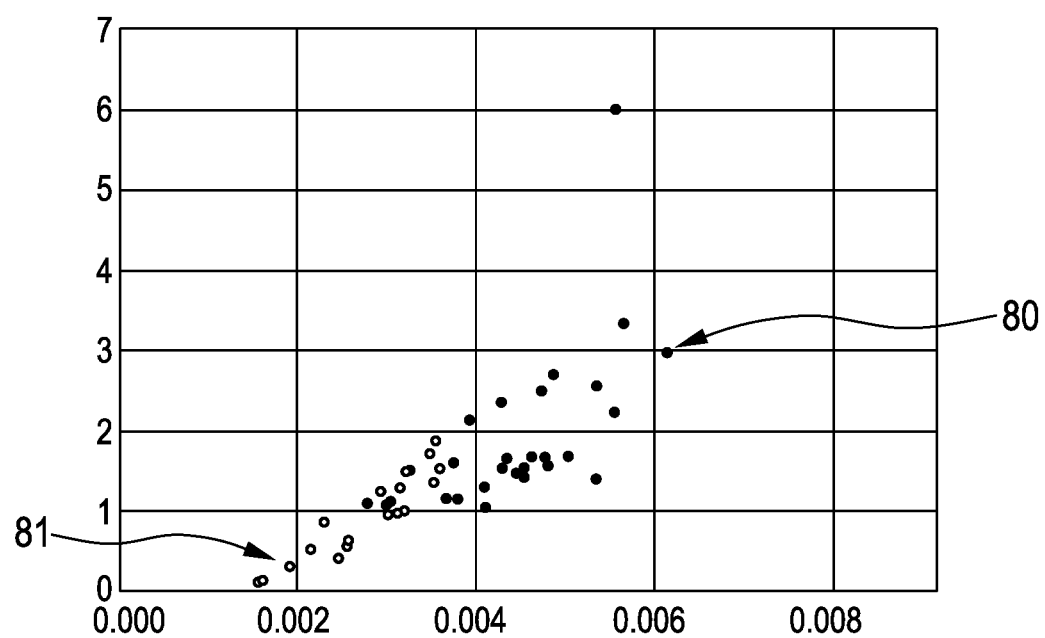
FIG. 7 illustrates exemplarily good registration results and bad registration results for different peakness strength values and different minimum mean curvature values.

In FIG. 7 the filled dots 80 are again the good registrations and the unfilled dots 81 are again the bad registrations, wherein on the vertical axis the peakness strength value is shown and on the vertical axis the minimum of the mean curvatures determined for the guidewire 32 and the catheter 33 is shown, i.e. the smaller one of a first mean curvature determined for the guidewire 32 and a second mean determined for the catheter 33. As can be seen in FIG. 7, a minimum of the mean curvatures being larger than 0.004 can indicate a good registration, i.e. can indicate that the corresponding current shapes are suitable for a shape-to-shape registration. The likelihood of reliably predicting that the registration will be good can be increased if the shapes are provided such that also the peakness strength value determined for the two shapes is larger than, for instance, 2.0. Thus, automatically by using a learning algorithm or manually by the person carrying out the calibration procedure respective thresholds can be predefined and later used by the suitability value determination unit for determining the second suitability value. Generally, if the combination of the second shape feature values indicates a region within the corresponding f-dimensional plot, wherein f indicates the number of second shape feature values used for determining the second suitability value, where unfilled dots are the majority, the suitability value determination unit determines a second suitability value indicating a predicted bad registration result and the user is informed via the output unit that the current shapes are not sufficient to get a robust, i.e.

unique, registration result. If the second shape feature values indicate a region within this f-dimensional space where filled dots are the majority, the suitability value determination unit determines that the current position and shapes are suitable for the subsequent shape-to-shape registration and, for instance, no warning is provided to the user via the output unit.

In an embodiment the output unit can be adapted to give a warning when the current shapes are not suitable for the registration. In such a setting seeing nothing means that the shapes are good for registration. It is of course possible that another type of information visualization can be provided. For example, the output unit can be adapted to provide a traffic light type of visualization that classifies the first shape feature values and/or the second shape feature values into three levels, wherein depending on which value the first suitability value and/or the second suitability value has, a green light, a red light or a yellow light can be shown.

Although in the above described embodiments the output unit is adapted to provide different colors for indicating the respective suitability, in other embodiments the output unit can be adapted to indicate the respective suitability in another way.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the first shape feature values, the determination of the second shape features values, the determination of the first suitability value, the determination of the second suitability value, the registration procedures, et cetera performed by one or several units or devices can be performed by any other number of units or devices. These procedures and/or the control of the assisting device in accordance with the assisting method and/or the control of the interventional system in accordance with the registration method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an assessing device for assessing the suitability of a shape of an instrument like a guidewire for a registration of a position and shape determination device like an optical shape sensing device with an imaging device. Curvature values being indicative of the curvature at several positions along the instrument are determined, which are used for determining shape feature values. These shape feature values are then used for determining a suitability value being indicative of the suitability of the shape of the instrument for the registration procedure, wherein an output is provided to a user based on the determined suitability value. The user can therefore modify the shape until the output indicates that the shape of the instrument is suitable for the registration, without requiring any image. This can reduce a radiation dose if the image is, for instance, an x-ray image.

The invention claimed is:

1. An assessing device for assessing a shape of an instrument, wherein the assessing device is configured to assess the suitability of the shape of the instrument for performing a registration procedure, wherein the shape has been determined by a position and shape determination device and is provided to the assessing device, and wherein the registration procedure relates to a registration of the position and shape determination device with an imaging device for imaging the instrument, wherein the assessing device comprises:
   a feature determination unit configured to: determine first shape feature values which depend on the position and shape of the instrument; determine curvature values being indicative of the curvature at several portions of the instrument at locations having predetermined distance; determine the first shape feature values based on the curvature values determine orientation difference values being indicative of the orientation differences of portions of the instrument at locations along the instrument having a predetermined distance to each other; determine a first number being indicative of the number of orientation difference values above a predetermined first threshold: determine a second number being indicative of the number of orientation difference values above a predetermined second threshold; and determine the orientation change value based on the first number and the second number;
   a suitability value determination unit configured to determine a first suitability value being indicative of the suitability of the shape of the instrument for the registration procedure based on the determined first shape feature values; and
   an output unit for providing an output to a user based on the determined first suitability value, wherein the feature determination unit is configured such that the first shape feature values include at least one of a maximum curvature value and an orientation change value being indicative of a change of orientation along the instrument.

2. The assessing device as defined in claim 1, wherein the suitability value determination unit is configured to determine the first suitability value such that it indicates a suitability class of a group of predefined suitability classes, which are indicative of different degrees of suitability of a shape of an instrument for the registration procedure, based on the determined first shape feature value, wherein a first suitability class indicates that the shape is not suitable and a second suitability class indicates that the shape is suitable, wherein the output unit is configured to provide different outputs for different suitability classes.

3. The assessing device as defined in claim 2, wherein the suitability value determination unit is configured to store the shape together with the determined suitability class such that, if the assessing device has been used with different shapes, different previous shapes together with corresponding previous suitability classes are stored, wherein the output unit is configured to show a representation of a stored previous shape together with the corresponding previous suitability class to the user.

4. The assessing device as defined in claim 1, wherein the feature determination unit is configured to determine the orientation change value depending on a weighted combination of the first number and the second number.

5. The assessing device as defined in claim 1, wherein the suitability value determination unit is configured to determine the first suitability value by comparing the first shape feature values with predefined shape feature value ranges.

6. The assessing device as defined in claim 1, wherein the assessing device is further configured to assess a suitability of the shape of the instrument for performing a registration procedure for registering the position and shape determination device with a further position and shape determination device for determining the position and shape of a further instrument, wherein:
   the feature determination unit is configured to determine curvature values being indicative of the curvature at several positions along the instrument and along the further instrument and to determine second shape feature values based on the curvature values of both instruments in the overlap region,
   the suitability value determination unit is configured to determine a second suitability value being indicative of the suitability of the shape of the instrument and of the further position and shape of the further instrument for the registration of the position and shape determination device with the further position and shape determination device based on the determined second shape feature values, and
   the output unit is configured to provide an output to the user based on the determined second suitability value.

7. The assessing device as defined in claim 6, wherein the feature determination unit is configured such that the second shape feature values include at least one of:
   a peakness strength value being indicative of a strength of a peak of a curvature match score, which is determined for different simulated relative positions of the instrument and hence its position and shape relative to the further instrument and hence its position and shape and which is indicative of a similarity of the curvature values of the instrument and the curvature values of the further instrument,
   a minimum curvature value as the minimum of the mean curvature values of the instrument and of the further instrument in an overlap region in which the instrument and the further instrument overlap, wherein the feature determination unit is configured to determine the overlap region based on the curvature values,
   a maximum curvature value as the maximum of the mean curvature values of the instrument and of the further instrument in the overlap region, and
   a total mean curvature value as the mean of the mean curvature values of the instrument and of the further instrument in the overlap region.

8. The assessing device as defined in claim 7, wherein, for determining the peak strength value, the feature determination unit is configured to:
   determine the simulated relative position of the instrument relative to the further instrument at which the curvature match score is maximal,
   determine difference values between the maximum curvature match score and curvature match scores determined for relative positions having a distance to the maximum relative position for which the maximum curvature match score has been determined, which is smaller than a predefined distance,
   determine a first sum of the difference values which have been determined for the relative positions being smaller than the maximum relative position and a second sum of the difference values which have been determined for the relative positions being larger than the maximum relative position, and determine the smaller one of the first sum and the second sum as the peak strength value.

9. An interventional system for performing an image-guided interventional procedure, the interventional system comprising:

an interventional instrument to be used within a subject, an imaging device constructed to image the interventional instrument within the subject, a position and shape determination device constructed to determine a position and shape of the interventional instrument within the subject, an assessing device constructed to assess a suitability of the shape of the interventional instrument for registering the position and shape determination device with the imaging device as defined by claim 1, wherein the position and shape determination device and the assessing device are configured to determine at least the shape of the instrument and to assess the suitability of the shape of the instrument, while a user at least modifies the shape of the instrument, an input unit for allowing a user to indicate that a registration of the position and shape determination device with the imaging device should start based on the current determined position and shape, and a registration device for registering the position and shape determination device with the imaging device based on the current determined position and shape of the interventional instrument and based on an image showing the interventional instrument with the current determined position and shape, if the user has indicated that the registration should start.

10. An assessing method for assessing a suitability of a shape of an instrument for performing a registration procedure, wherein the position and shape has been determined by a position and shape determination device for determining a position and shape of an instrument and wherein the registration procedure relates to a registration of the position and shape determination device with an imaging device for imaging the instrument, wherein the assessing method comprises:

determining first shape feature values which depend on the shape of the instrument by a feature determination unit, wherein the feature determination unit determines curvature values being indicative of the curvature at several portions of the instrument at locations having predetermined distance and determines the first shape feature values based on the curvature values, determining a first suitability value being indicative of the suitability of the shape of the instrument for the registration procedure based on the determined first shape feature values by a suitability value determination unit;

determining orientation difference values being indicative of the orientation differences of portions of the instrument at locations along the instrument having a predetermined distance to each other;

determining a first number being indicative of the number of orientation difference values above a predetermined first threshold;

determining a second number being indicative of the number of orientation difference values above a predetermined second threshold;

determining the orientation change value based on the first u and the second number, and providing an output to a user based on the determined first suitability value by an output unit, wherein the first shape feature values include at least one of a maximum curvature value and an orientation change value being indicative of a change of orientation along the instrument.

11. A registration method for registering a position and shape determination device for determining the position and shape of an instrument with an imaging device for generating an image of the instrument, wherein the registration method includes:

determining a position and shape of the instrument by using the position and shape determination device and assessing a suitability of the shape of the instrument for registering the position and shape determination device with the imaging device as defined in claim 10, while a user modifies at least the shape of the instrument, and allowing the user to indicate that the registration should start based on the current position and shape and registering the position and shape determination device with the imaging device, if the user has indicated that the registration should start based on the current position and shape.

12. A tangible, non-transitory computer readable medium comprising a computer program for causing a computer to perform steps for assessing a suitability of a shape of an instrument for performing a registration procedure, the computer program comprising program code for causing an assessing device to carry out the steps of the assessing method as defined in claim 10, when the computer program is run on a computer controlling the assessing device.

13. A tangible, non-transitory computer readable medium comprising a computer program for causing a computer to perform steps for registering a position and shape determination device for determining the position and shape of an instrument with an imaging device for generating an image of the instrument, the computer program comprising program code for causing an interventional system a to carry out the steps of the registration method as defined in claim 11, when the computer program is run on a computer controlling the interventional system.

* * * * *